(12) United States Patent
Rossi et al.

(10) Patent No.: US 11,628,002 B2
(45) Date of Patent: Apr. 18, 2023

(54) BONE PLATING SYSTEM CLAMP SIZING INSTRUMENT AND INSTALLATION INSTRUMENT

(71) Applicant: DEPUY SYNTHES PRODUCTS, INC., Raynham, MA (US)

(72) Inventors: Danielle Rossi, West Chester, PA (US); Diana Castillo Sanchez, West Chester, PA (US); Kenny Koay, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 68 days.

(21) Appl. No.: 17/366,400

(22) Filed: Jul. 2, 2021

(65) Prior Publication Data
US 2022/0061897 A1  Mar. 3, 2022

Related U.S. Application Data

(60) Provisional application No. 63/069,990, filed on Aug. 25, 2020.

(51) Int. Cl.
*A61B 17/80* (2006.01)
*A61B 17/88* (2006.01)
(Continued)

(52) U.S. Cl.
CPC ........ *A61B 17/808* (2013.01); *A61B 17/8004* (2013.01); *A61B 17/8019* (2013.01);
(Continued)

(58) Field of Classification Search
CPC .......... A61B 2017/681; A61B 17/8004; A61B 17/8019; A61B 17/808; A61B 17/82;
(Continued)

(56) References Cited

U.S. PATENT DOCUMENTS

| 1,985,108 A | 12/1933 | Rush |
| 2,362,957 A | 9/1941 | Hackett |

(Continued)

OTHER PUBLICATIONS

U.S. Appl. No. 16/804,544, filed Feb. 28, 2020 Kenny Koay, et al.
(Continued)

*Primary Examiner* — Larry E Waggle, Jr.
(74) *Attorney, Agent, or Firm* — Kramer & Amado, P.C.

(57) ABSTRACT

A measuring instrument configured to measure a bone and a plate to determine the size of an attachment clamp, including: a medial clamp configured to engage a medial portion of the bone; a medial gauge connected to the medial clamp, the medial gauge including: a key along a portion of the medial gauge adjacent the medial clamp; a gauge indicator configured to indicate the size of attachment clamp; and a threaded portion; a lateral clamp configured to engage a plate on the bone, where the lateral clamp has a hollow portion with a channel, wherein the gauge indicator is positioned in the hollow portion and wherein the channel is configured to engage the key of the gauge indicator to prevent the lateral clamp from rotating about the gauge indicator; and a tightening knob threaded onto the thread portion of the of the medial gauge, wherein one end of the tightening knob indicates on the gauge indicator the size of the attachment clamp.

13 Claims, 16 Drawing Sheets

(51) Int. Cl.
  *A61B 90/00* (2016.01)
  *A61B 90/92* (2016.01)

(52) U.S. Cl.
  CPC .......... *A61B 17/8057* (2013.01); *A61B 17/88* (2013.01); *A61B 17/8872* (2013.01); *A61B 17/8875* (2013.01); *A61B 90/06* (2016.02); *A61B 90/92* (2016.02); *A61B 2090/066* (2016.02)

(58) Field of Classification Search
  CPC . A61B 17/88; A61B 17/8869; A61B 17/8872; A61B 17/8875
  See application file for complete search history.

(56) References Cited

U.S. PATENT DOCUMENTS

| | | | |
|---|---|---|---|
| 2,427,128 A | 1/1946 | Ettinger | |
| 3,835,849 A | 9/1974 | McGuire | |
| 4,187,840 A | 2/1980 | Watanabe | |
| 5,015,248 A | 5/1991 | Burstein et al. | |
| 5,201,736 A | 4/1993 | Strauss | |
| 5,690,640 A | 11/1997 | Gotfried | |
| 5,797,915 A | 8/1998 | Pierson, III et al. | |
| 5,928,231 A | 7/1999 | Klein et al. | |
| 6,443,507 B1 | 9/2002 | Korvemaker | |
| 7,883,532 B2 | 2/2011 | Biscup et al. | |
| 8,083,780 B2 | 12/2011 | McClellan, III et al. | |
| 8,685,037 B1 | 4/2014 | Jordan | |
| 8,696,670 B2 | 4/2014 | Chico Roca | |
| 8,721,645 B2 | 5/2014 | Belliard | |
| 8,790,344 B1 | 7/2014 | Foerster | |
| 8,936,628 B2 | 1/2015 | Anderson | |
| 9,504,503 B2 | 11/2016 | Cavallazzi et al. | |
| 9,566,104 B2 | 2/2017 | Kohler | |
| 10,179,001 B2 | 1/2019 | Hashmi et al. | |
| 11,213,329 B2 * | 1/2022 | Koay | A61B 17/68 |
| 11,304,735 B2 * | 4/2022 | Sayger | A61B 17/7225 |
| 2008/0009871 A1 | 1/2008 | Orbay et al. | |
| 2008/0097450 A1 | 4/2008 | Brown | |
| 2010/0114154 A1 | 5/2010 | Snell | |
| 2011/0054547 A1 | 3/2011 | Anderson | |
| 2012/0290017 A1 | 11/2012 | Haidukewych | |
| 2013/0116733 A1 * | 5/2013 | Stoll, Jr. | A61B 17/8866 606/282 |
| 2013/0131738 A1 | 5/2013 | Powell et al. | |
| 2014/0194907 A1 | 7/2014 | Bonutti et al. | |
| 2014/0243841 A1 | 8/2014 | Cavallazzi | |
| 2015/0209093 A1 | 7/2015 | Dallis | |
| 2016/0095636 A1 | 4/2016 | Wiederkehr | |
| 2017/0035476 A1 | 2/2017 | Cavallazzi | |
| 2019/0159819 A1 | 5/2019 | Fatone et al. | |

OTHER PUBLICATIONS

Synthes 2011 Trauma Catalog; Instruments and Implants Improved by AO Foundation printed May 2011; 75pgs.

* cited by examiner

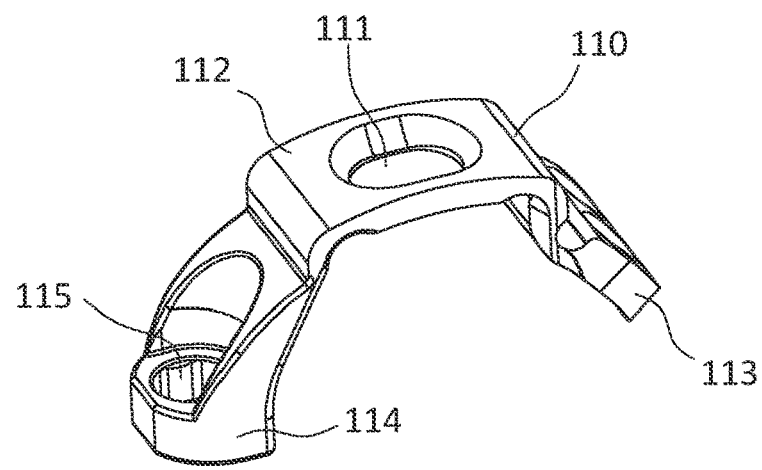
FIG. 1B
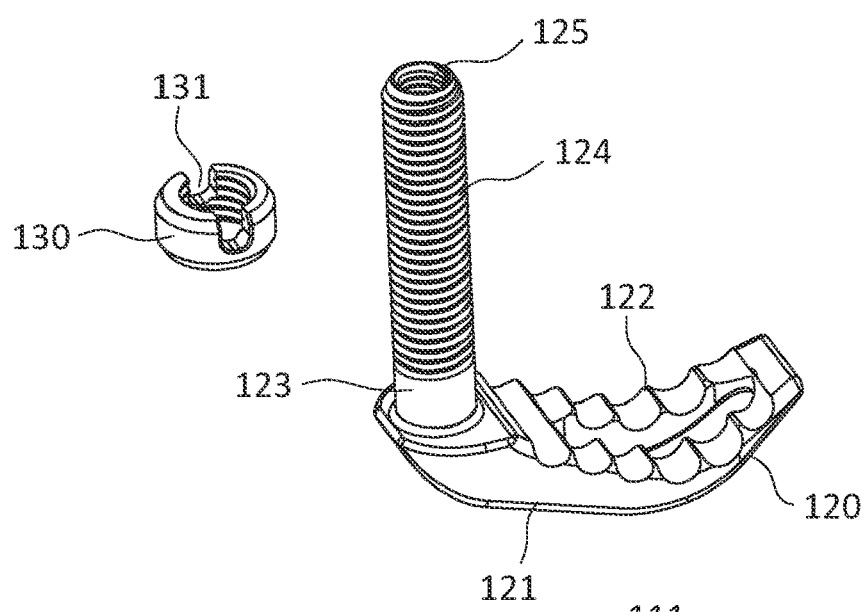
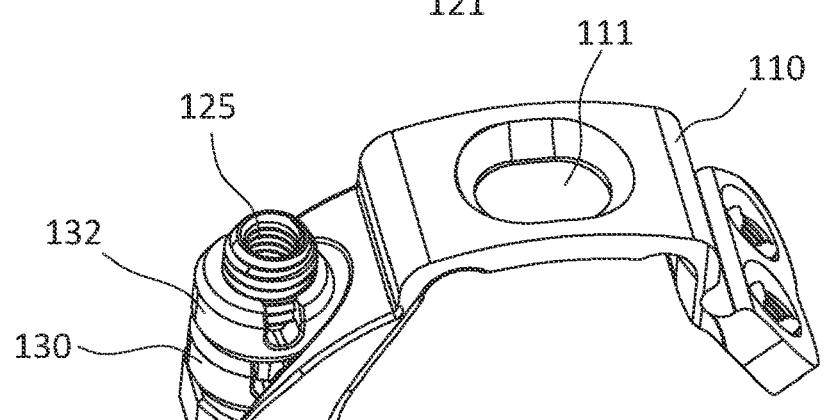
FIG. 1C
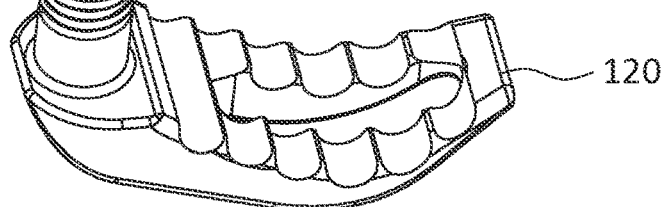

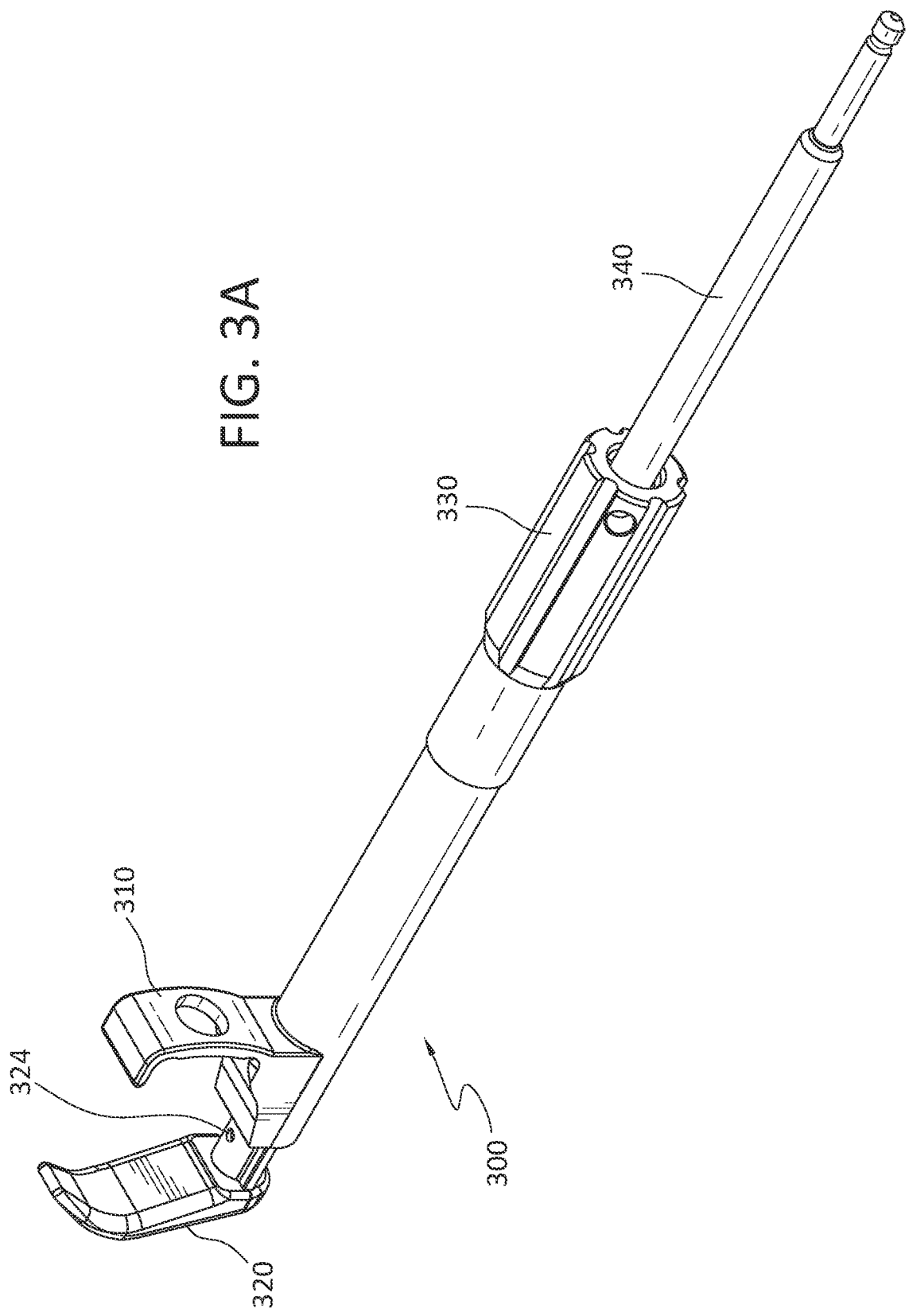

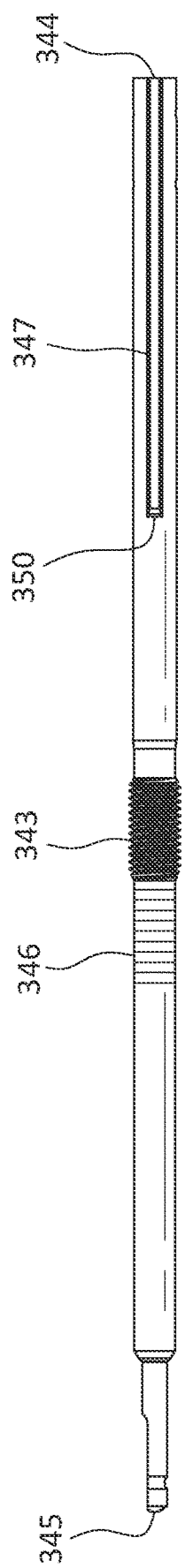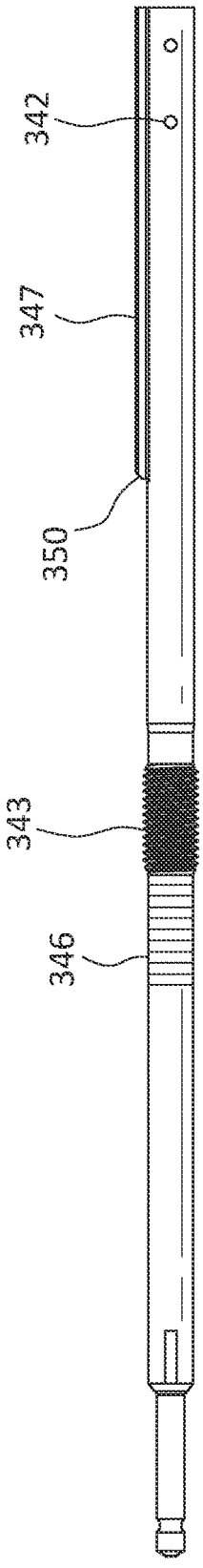
FIG. 7B
FIG. 7C

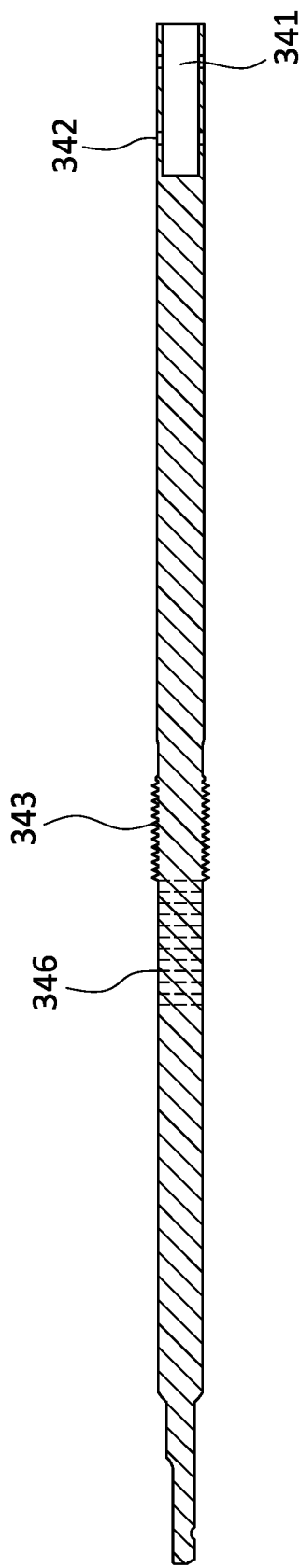
FIG. 7E
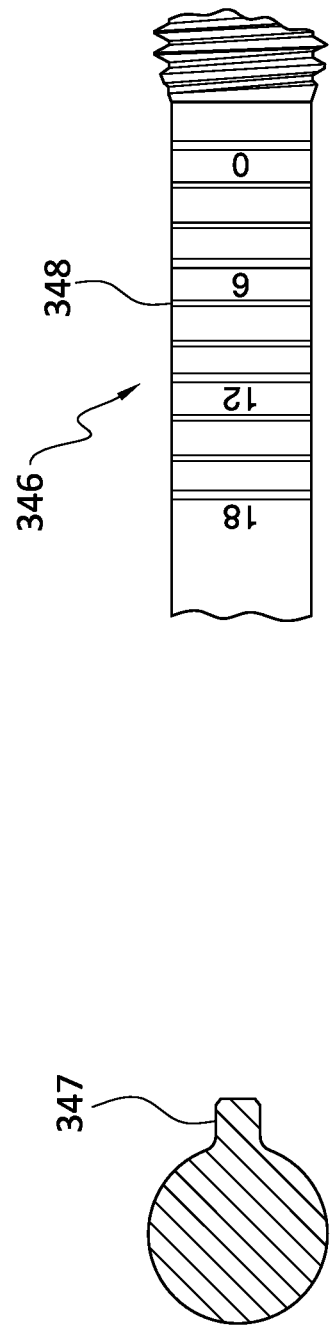
FIG. 7D
FIG. 7F

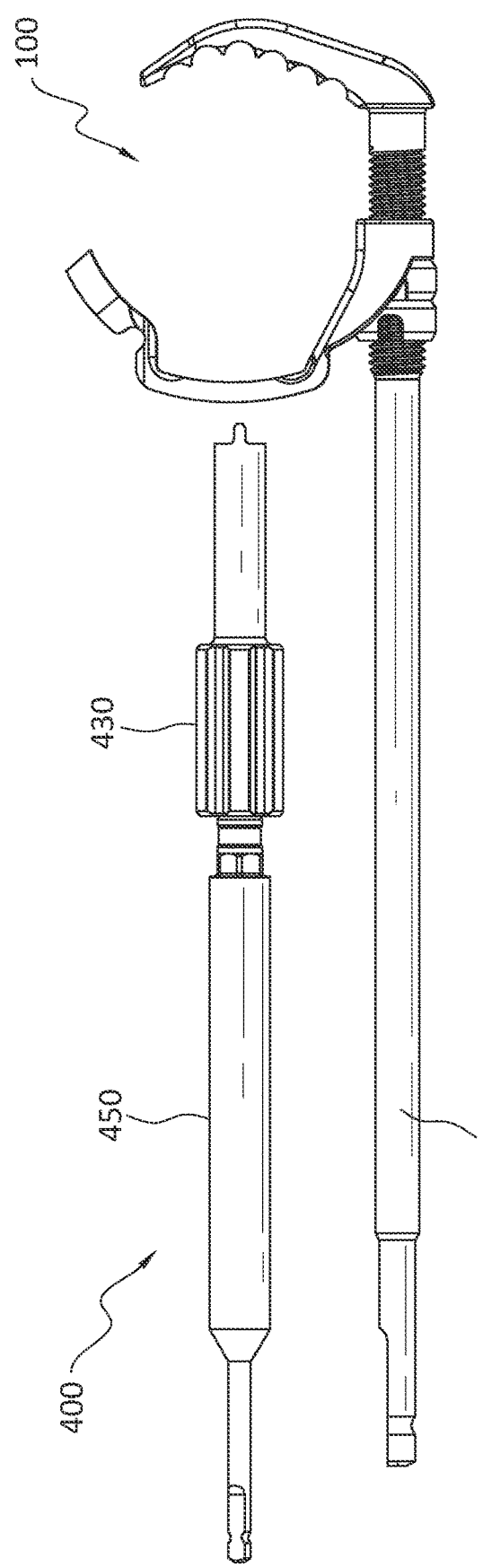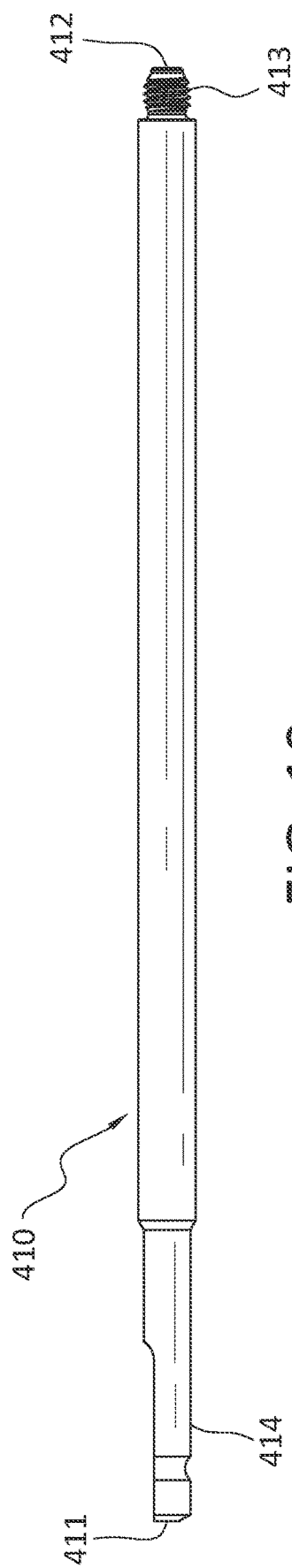

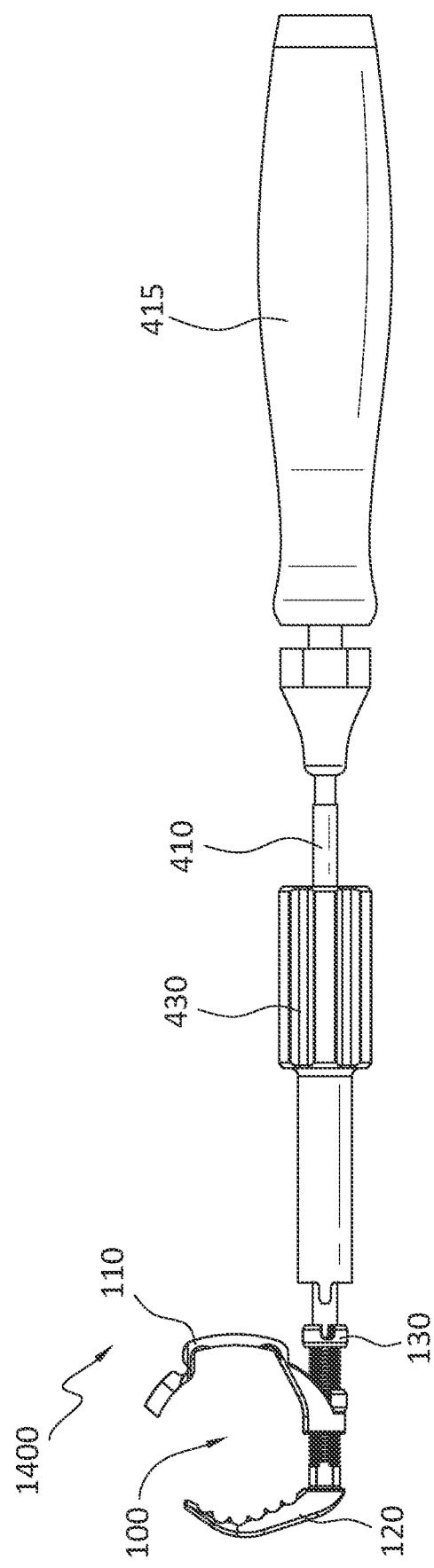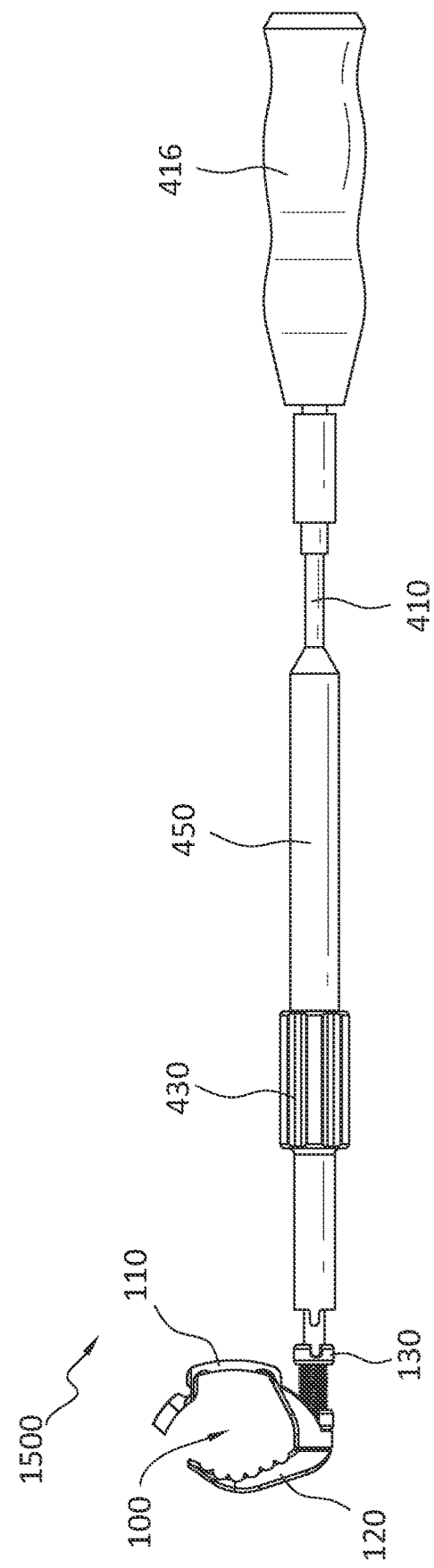

BONE PLATING SYSTEM CLAMP SIZING INSTRUMENT AND INSTALLATION INSTRUMENT

CROSS-REFERENCE TO RELATED APPLICATIONS

This application claims benefit to U.S. Provisional Patent Application No. 63/069,990 filed on Aug. 25, 2020, the contents of which are hereby incorporated bFfig.y reference for all purposes as if fully set forth herein.

TECHNICAL FIELD

Various exemplary embodiments disclosed herein relate generally to a bone plating system clamp sizing instrument and installation instrument.

BACKGROUND

In some cases, fractures of long bones may be treated using bone fixation devices positioned on an outer surface of the bone. For example, the fixation of oblique fractures in long bones previously fitted with metal prostheses such as, for example, an intramedullary nail and/or a femoral stem, may preclude the use of bone fixation devices that extend into the bone if, for example, the previously inserted prosthesis would interfere with proper insertion of one or more of the fixation devices. Such bone fixation procedures therefore often use a combination of cables and metal compression plates employed with or without fixation screws that extend into the bone. After fixation, however, bone resorption may cause cables to lose their effectiveness.

For example, a periprosthetic fracture (PPFx) of the femur may occur both intra-operatively and post-operatively. Type B fractures, i.e., fractures around or directly below a stable or loose stem are the most common proximal femur periprosthetic fractures. The treatment of these fractures can be particularly challenging due to limited bone for stable fixation, the type of hip stem, the stem's stability and other patient comorbidities. This leads to limited options for peri-implant fixation. To combat this problem, a periprosthetic modular femoral plating system will allow surgeons to connect several devices in various configuration to promote peri-implant fixation.

The modular plating system may include a plate and an attachment clamp. The attachment clamp is an alternative solution to a cable. It may for example provide fixation in the proximal segment of periprosthetic Type B fracture when used in conjunction with a femur plate.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a measuring instrument configured to measure a bone and a plate to determine the size of an attachment clamp, including: a medial clamp configured to engage a medial portion of the bone; a medial gauge connected to the medial clamp, the medial gauge including: a key along a portion of the medial gauge adjacent the medial clamp; a gauge indicator configured to indicate the size of attachment clamp; and a threaded portion; a lateral clamp configured to engage a plate on the bone, where the lateral clamp has a hollow portion with a channel, wherein the gauge indicator is positioned in the hollow portion and wherein the channel is configured to engage the key of the gauge indicator to prevent the lateral clamp from rotating about the gauge indicator; and a tightening knob threaded onto the thread portion of the of the medial gauge, wherein one end of the tightening knob indicates on the gauge indicator the size of the attachment clamp.

Various embodiments are described, wherein the key further includes a key end that is the end of the key away from the medial arm, and the lateral arm further includes a cut out at an edge of the hollow portion, wherein the cut out is configured to engage the key end to keep the lateral arm in an open position away from the medial arm.

Various embodiments are described, wherein the cut out is positioned at a different angular position along a circumference of the hollow portion than the channel.

Various embodiments are described, wherein the angular position is about 90 degrees.

Various embodiments are described, wherein the gauge indicator includes a plurality lines and numbers indicating the size of the attachment clamp.

Various embodiments are described, wherein the gauge indicator includes a plurality of color coded bands indicating the size of the attachment clamp.

Various embodiments are described, wherein the lateral clamp includes an arm member with an arm opening.

Various embodiments are described, wherein the tightening knob includes a wrench hole configured to accept a wrench to torque the tightening knob.

Various embodiments are described, wherein the tightening knob includes double-lead threads.

Further various embodiments relate to a method of using a measuring instrument to measure a bone and a plate to determine the size of an attachment clamp, including: placing a medial clamp of the measuring instrument on a medial portion of the bone; sliding a lateral clamp along a medial gauge of the measuring instrument into contact with the plate; rotating a tightening knob of the measuring instrument to tighten the lateral clamp against the plate; and determining the size of the attachment clamp based upon the location of the tightening knob over a gauge indicator of the medial gauge.

Various embodiments are described, further including before sliding a lateral clamp along a medial gauge: disengaging a cut out on the lateral clamp from an end of a key on the medial gauge; rotating the lateral clamp until a channel in the lateral clamp aligns with the key on the medial gauge.

Various embodiments are described, wherein rotating a tightening knob further includes reducing a fracture of the bone.

Various embodiments are described, wherein determining the size of the attachment clamp further includes identifying a color code associated with the size of the clamp.

Various embodiments are described, wherein determining the size of the attachment clamp further includes reading a number off of the gauge indicator indicating the size of the clamp.

Various embodiments relate to an insertion instrument configured to insert clamp on a bone and a plate, including: an attachment clamp including: lateral clamp with a hollow opening; a medial clamp attached to a stud wherein the stud has a threaded opening; and the stud is located inside the hollow opening of the lateral clamp; and a first clamp nut on the stud, wherein the clamp nut has a nut slot; a connection rod with a distal end having a threaded connector configured to be screwed into the threaded opening of the stud; a provisional nut driver including: a central hollow opening configured to accept the connection rod therethrough: a tang at a distal end configured to engage the nut slot: an opening at a proximal end including a drive interface; a spring channel in the central hollow opening; and a spring in the spring channel; and a final nut driver including: a body with a hollow opening configured to receive a proximal end of the connection rod; a ridge around the circumference of a distal end of the final nut driver configured to be inserted into the opening of the provisional nut driver; a final nut driver interface between the ridge and the body configured to engage the driver interface of the driver interface of the provisional nut driver; and a handle connector at a proximal end of the final nut driver.

Various embodiments are described, wherein the drive interface and the final nut driver interface have corresponding polygonal shapes.

Various embodiments are described, wherein the hollow opening has a first section configured to receive an end portion of the stud.

Various embodiments are described, wherein the hollow opening has a second section configured to receive the connection rod therethrough.

Various embodiments are described, wherein the hollow opening has a third section configured to receive a distal of the final nut driver.

Various embodiments are described, wherein the hollow opening has a first section configured to receive an end portion of the stud, a second section configured to receive the connection rod therethrough, and a third section configured to receive a distal of the final nut driver.

Various embodiments are described, wherein the attachment clamp includes a second clamp nut with nut slot.

Various embodiments are described, further including a non-torque limiting handle configured to engage a proximal end of the connection rod.

Various embodiments are described, further including a torque limiting handle configured to engage the handle connector of the final nut driver.

Various embodiments relate to a method of inserting an attachment clamp using a insertion instrument to clamp a plate to a bone, including: attaching a connection rod of the insertion tool to a hollow opening in stud of the attachment clamp; provisionally tightening a first nut of the attachment clamp using a provisional nut driver by engaging a tang on the provisional nut driver with a nut slot in the first nut and rotating the provisional nut driver; attaching a lateral clamp of the attachment clamp to the plate using a connector; attaching a final nut driver to the provisional nut driver; and tightening the first clamp nut to a specified torque value by rotating a torque handle connected to the final nut driver.

Various embodiments are described, further including before attaching a final nut driver to the provisional nut driver, removing a non-torque limiting handle from a proximal end of the connection rod.

Various embodiments are described, wherein attaching a lateral clamp of the attachment clamp to the plate using a connector further includes screwing a screw into the plate through an opening in the lateral clamp.

Various embodiments are described, further including removing an assembly including the torque limiting handle, the final nut driver, and the provisional nut driver; placing a second clamp nut with a nut slot over the connection rod onto the stud of the attachment clamp; replacing the assembly over the connection rod; and tightening the second clamp nut to a specified torque using the torque limiting handle.

BRIEF DESCRIPTION OF THE DRAWINGS

In order to better understand various exemplary embodiments, reference is made to the accompanying drawings, wherein:

FIG. 1B illustrates an exploded view of the attachment clamp;

FIG. 1C illustrates a top perspective view of the attachment clamp using two nuts;

FIGS. 3A, 3B, and 3C illustrate perspective, side, and cross-sectional views respectively of an attachment clamp sizing tool;

FIGS. 7A-7F illustrate various views of the medial gauge;

FIG. 9. illustrates an insertion instrument;

FIG. 10 illustrates the connection rod;

FIG. 14 illustrates an assembly including the attachment clamp, connection rod, provisional nut driver, and non-torque limiting handle; and FIG. 15 illustrates an assembly including the attachment clamp, connection rod, provisional nut driver, final nut driver, second clamp nut, and torque limiting handle.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Figure 1A:
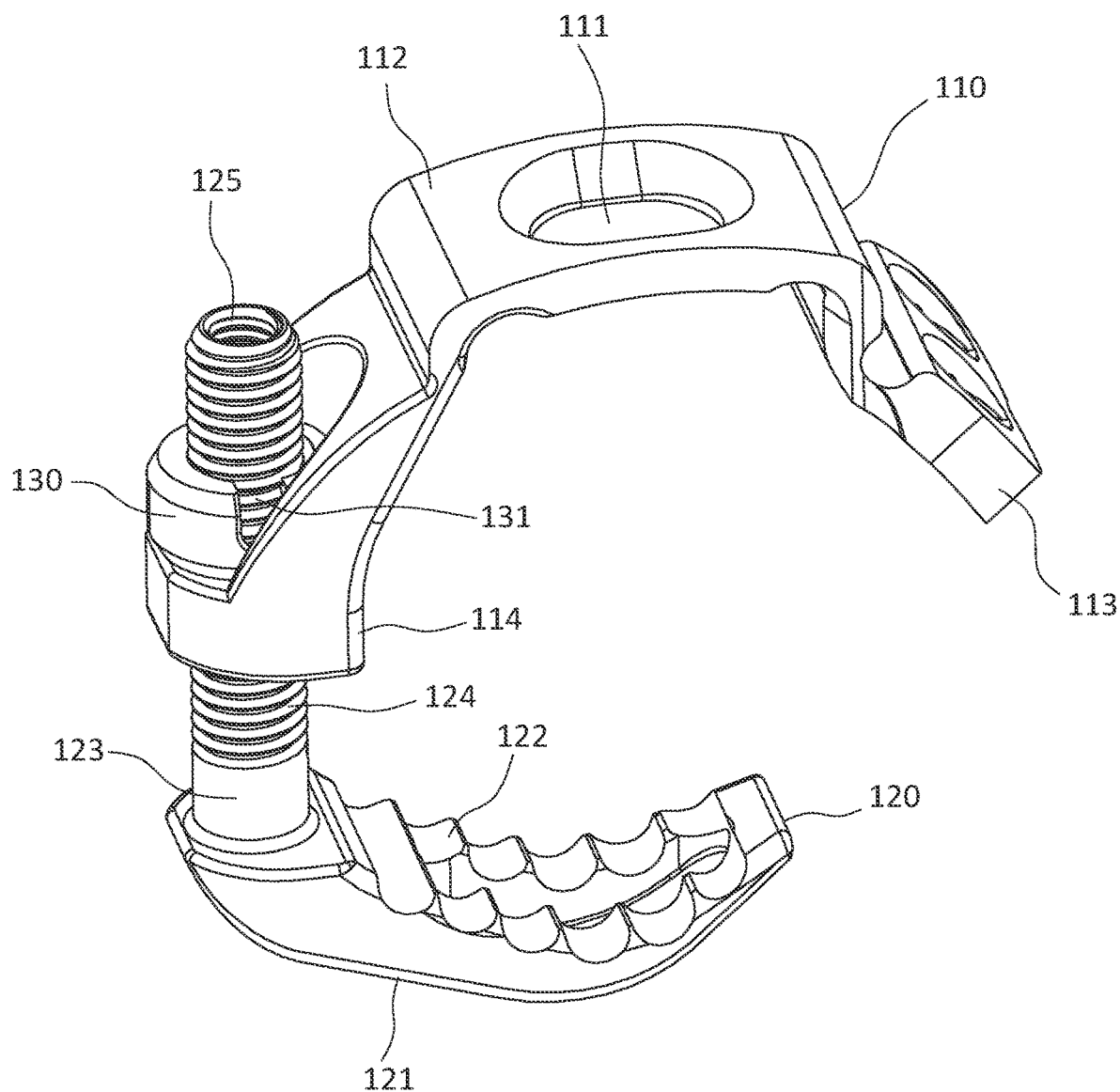
FIG. 1A illustrates a perspective view of the attachment clamp.

FIG. 1A illustrates a perspective view of the attachment clamp 100. FIG. 1B illustrates an exploded view of the attachment clamp 100. FIG. 1C illustrates a top perspective view of the attachment clamp using two nuts. The attachment clamp 100 includes a lateral clamp 110, a medial clamp 120, and a nut 130.

The medial clamp 120 includes a medial clamp arm 121 attached to a stud 123. The medial clamp arm 121 may include teeth 122 or some other gripping feature that securely engage the bone to be clamped. The medial arm 121 has a curved shape that follows the general curve of the bone to be repaired. Also, the size of the medial arm 121 is sized to accommodate the size of the bone to be repaired. The stud 123 has a threaded portion 124 that accepts the nut 130. In an alternative embodiment, the length of the stud 123 may be sized to accommodate the size of the bone to be repaired. The end of the stud 123 has an stud opening 125. The stud opening 125 is shown as including internal threads that are configured to accept a threaded portion of an attachment clamp insertion tool as will be described below.

The lateral clamp 110 includes a first end 114, a second end 113, and a central portion 112. The central portion 112 includes a screw hole 111. During installation of the attachment clamp 100, the screw hole 111 is aligned with a screw hole on the plate, and a screw is inserted to secure the attachment clamp 100 to the plate. The central portion 110 of the lateral clamp 120 is generally shaped to conform with the shape of the plate. This shape of the central portion 110 along with the screw allows the attachment clamp 100 to securely engage and fix the plate to the bone to be repaired. The first end 114 of the lateral clamp 110 includes a lateral clamp opening 115. The lateral clamp opening 115 accepts the stud 123 therethrough. Then the nut 130 may be threaded onto the stud 123 to draw lateral clamp 110 and the medial clamp 120 towards one another to thereby clamp the plate to the bone to be repaired. FIG. 1C illustrates the use of two nuts 130, 132 on the stud 123. In situations where there are concerns that a single nut 130 may be prone to backing off, the second nut 132 may be used to prevent back off of the first nut 130.

Figure 2A:
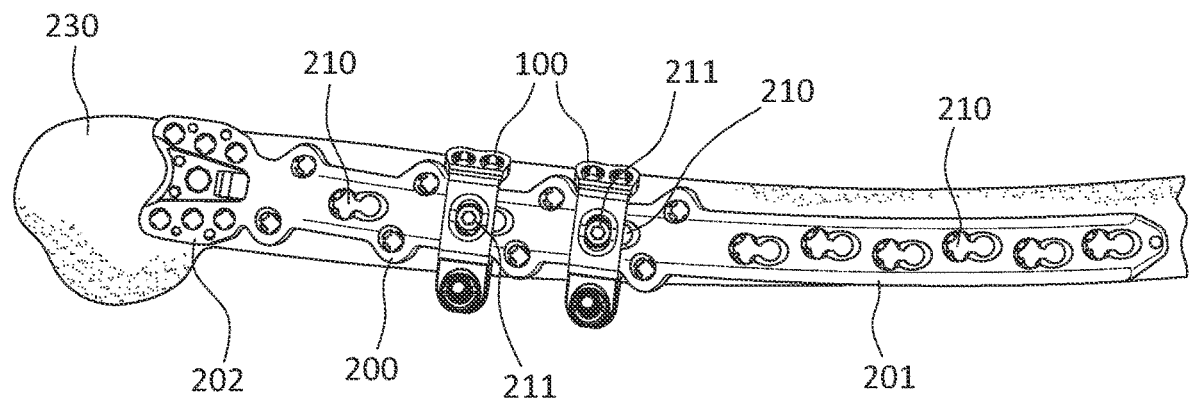
FIG. 2A illustrates the attachment clamp clamping the plate to a bone.
Figure 2B:
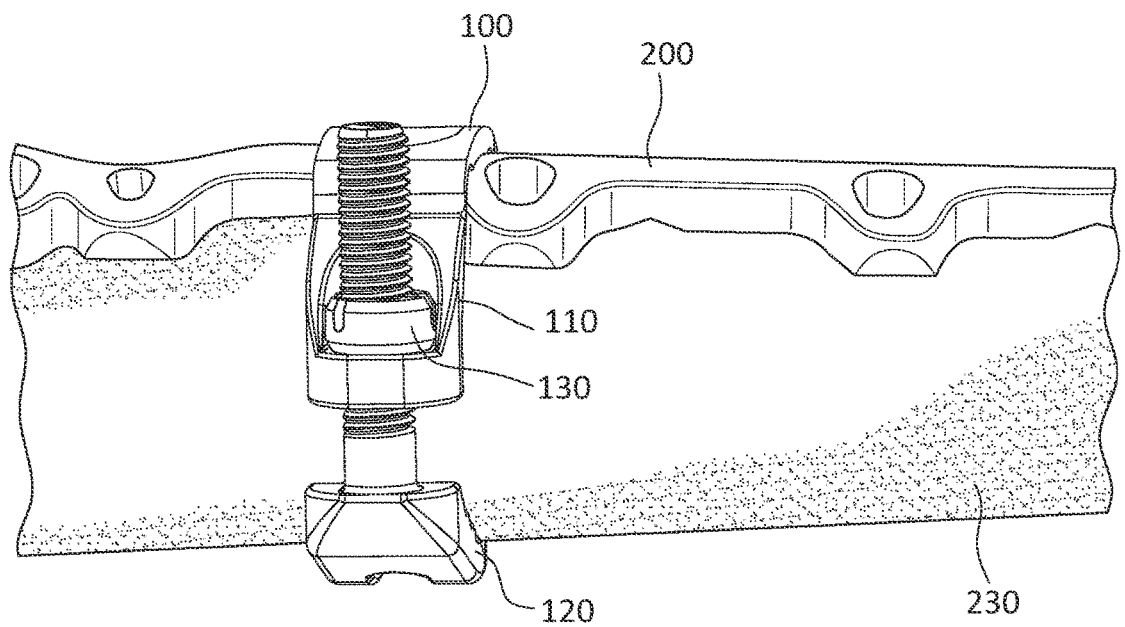
FIG. 2B illustrates an expanded side view of the attachment clamp 100 clamping the plate 200 to the bone.

FIG. 2A illustrates the attachment clamp 100 clamping the plate 200 to a bone 230. FIG. 2B illustrates an expanded side view of the attachment clamp 100 clamping the plate 200 to the bone 230. The plate 200 shown in FIG. 2A is for attachment to the femur 230, but other types of plates with different shapes and applications may also be used. The plate 200 includes a body 201 that extends along the shaft of the femur 200. The plate 200 also includes a head 202 that is adapted to the shape of the upper part of the femur 200. While the plate 200 shown is for use on fractures of the femur, the plate 200 may take various shapes depending the specific application and the associated anatomy. The plate 200 includes screw holes 210 that accept a screw 211 as described above to fix the attachment clamp 100 to the plate 200. The screw holes 210 may include threads that accept the threads of the screw 211. The screws 211 may be variable angle locking screws and the screw holes 210 and 111 may be designed to accept such screws 211. In this case, the screw hole 111 will have threads as well to facilitate the variable angle locking of the screw 211. In another embodiment, a screw and insert may be used to connect the attachment clamp 100 to the plate. The insert may have internal and external threads, and the insert may be threaded into the screw hole 210. The screw 211 may then be threaded into the insert.

The plate 200, attachment clamp 100, and screws 211 may be manufactured from any type of surgical grade material. For example, the material may be titanium or a surgical grade stainless steel.

Additional embodiments of attachment clamps and associated bone plates are described in Patent Application Nos. xxxx, filed xxx and xxxx, filed xxxx, which are hereby incorporated by reference for all purposes as if fully set forth herein.

The attachment clamp 100 may come in different sizes to be used based upon the specific anatomy of the patient. For example, in the case of a femoral plate and attachment clamp, three different sizes may be available for use. During surgery the surgeon needs to determine which size attachment clamp will be needed for the patient. Specifically, the medial clamp 120 may come in three sizes and be chosen by the surgeon at the time of the surgery. This may be done using generic measuring tools, but access to the surgical site to make the measurement would be difficult using a generic tool. In response to this need, embodiments of an attachment clamp sizing tool will be described.

Figure 3B:
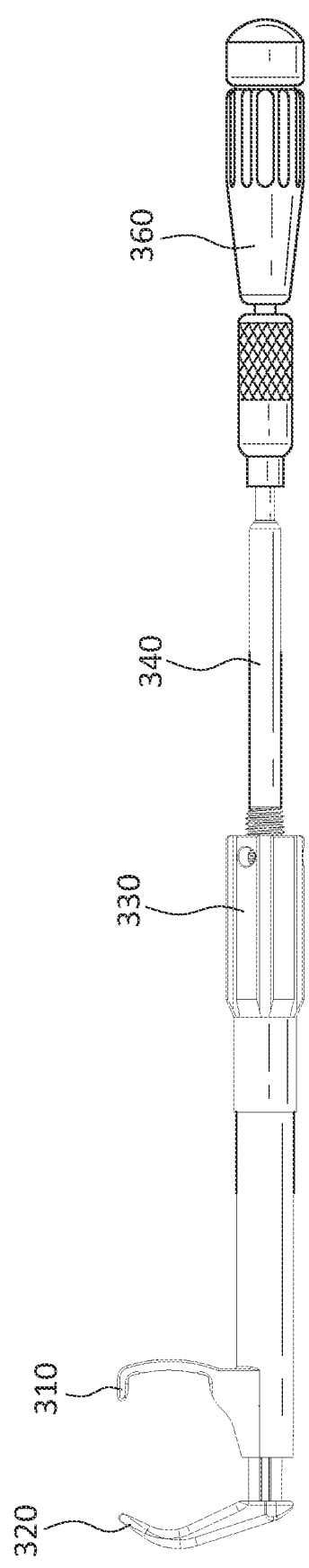
Figure 3C:
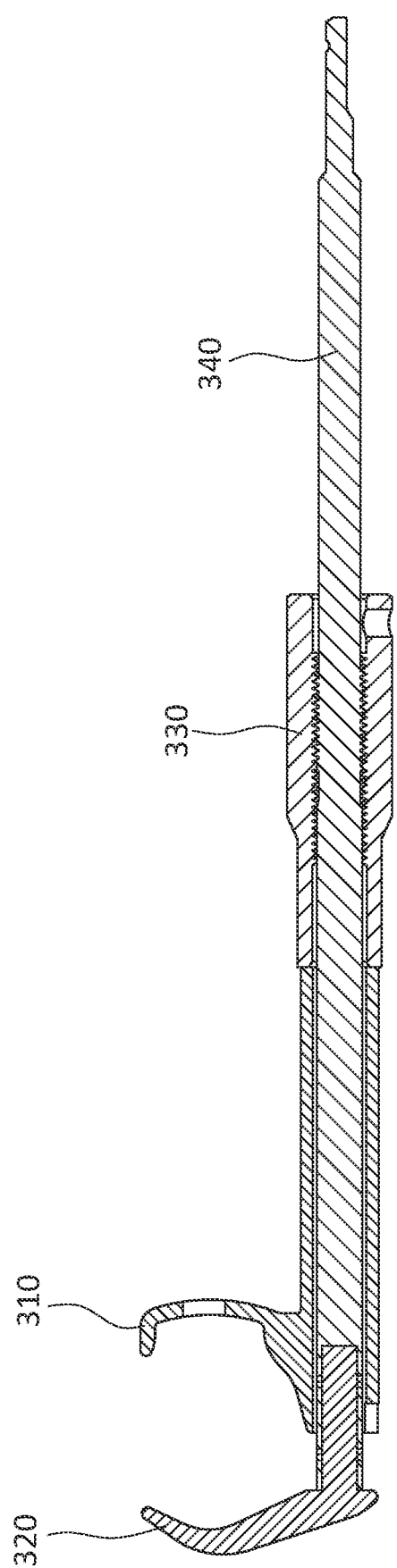

FIGS. 3A, 3B, and 3C illustrate perspective, side, and cross-sectional views respectively of an attachment clamp sizing tool. The sizing tool 300 includes medial arm 320, a lateral arm 310, a tightening knob 330, a medial gauge 340, and a handle 360.

Figure 4A:
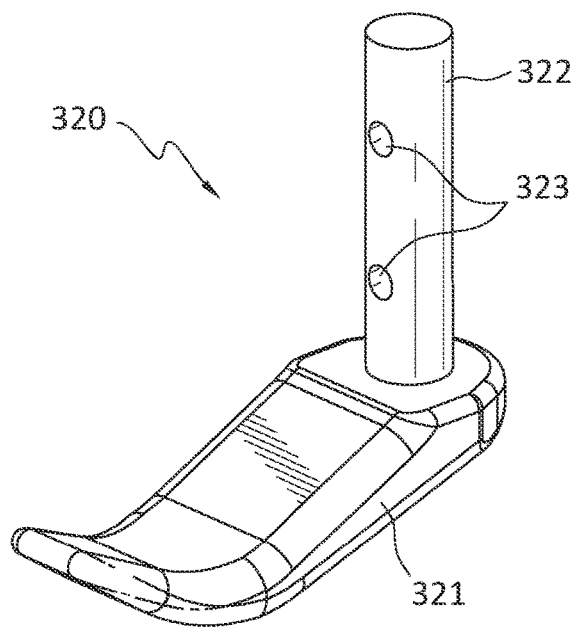
FIGS. 4A and 4B illustrate perspective and side views respectively of the medial arm of the attachment clamp sizing tool.
Figure 4B:
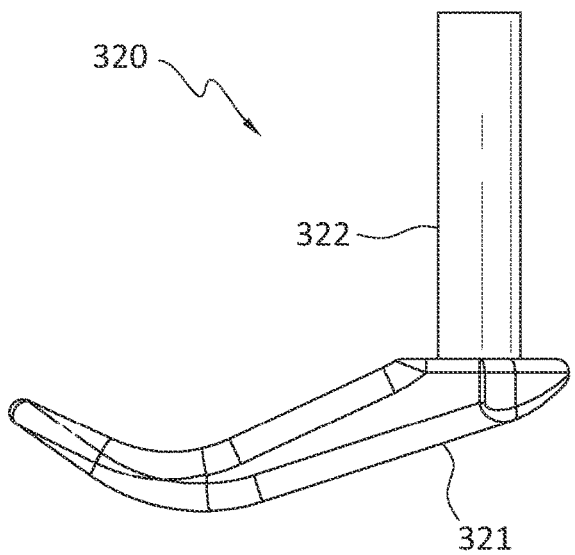

FIGS. 4A and 4B illustrate perspective and side views respectively of the medial arm 320. The medial arm 320 includes a body 321 that has a shape that mimics the shape of the medial clamp 120. The medial arm 320 also has a shaft 322 extending from the body 321. The shaft 322 includes two openings 323 (although a different number of openings may be used). The shaft 322 fits within a hollow end 341 of the medial gauge 340 (see FIGS. 7C and 7E) and may be secured to the medial gauge 340 with pins 324 inserted through holes 323 on the shaft 322 and holes 342 on the medial gauge 340. In other embodiments, the medial arm 300 and the medial gauge 340 may be manufactured as a single part.

Figure 5A:
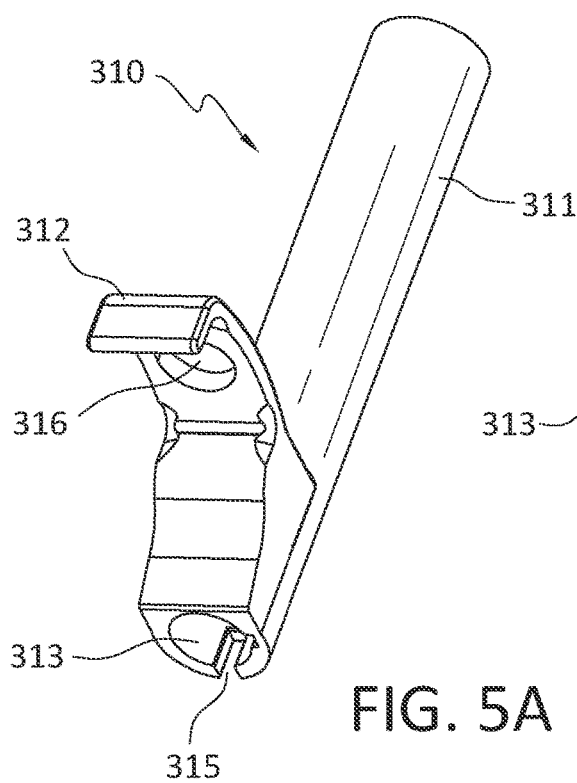
FIGS. 5A and 5B illustrate perspective and side cross-sectional views respectively of the lateral arm of the attachment clamp sizing tool.
Figure 5B:
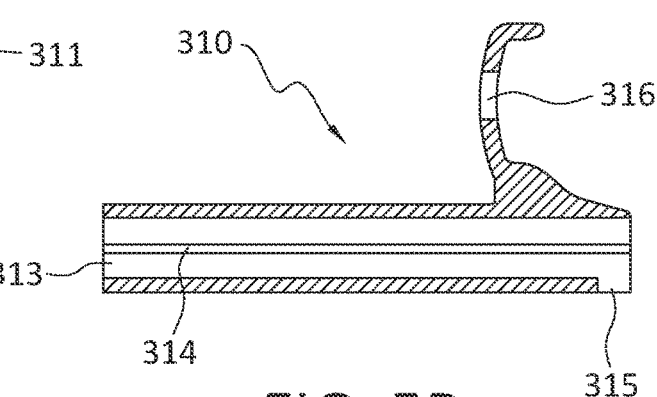

FIGS. 5A and 5B illustrate perspective and side cross-sectional views respectively of the lateral arm 310. The lateral arm 310 includes an arm member 312 extending from a tubular body 311. The arm member 312 has a shape that generally mimics the shape of the lateral clamp 110. The arm member 312 may have an arm hole 316 that allows the surgeon to observe when the arm member 312 approaches and contacts the plate as well as allowing for the surgeon to identify hole to hole alignment for proper placing of the sizing instrument. The lateral arm 310 includes a central opening 313 that accepts the medial gauge 340. Inside the central opening 313, the lateral arm 310 also includes a channel 314 that runs along the length of the central opening 313 and is configured to interact with the medial gauge 340 as will be described below. The lateral arm 310 also includes a cut out 315 which is an opening of the tubular body 311 at an end of the tubular body 311. As shown in FIGS. 5A and 5B, the cut out 315 is shown as a rectangular opening, but other shapes are possible as well. The cut out 315 is shown as being angularly displaced by 90° around the circumference of the tubular body 311 from the channel. Other angular displacements are possible as well. As will be further described below, the cut out 315 is configured to engage a portion of the medial gauge 340 to keep the lateral arm 310 away from the plate 200 and bone 230 during the initial placement of the sizing instrument 300.

Figure 6A:
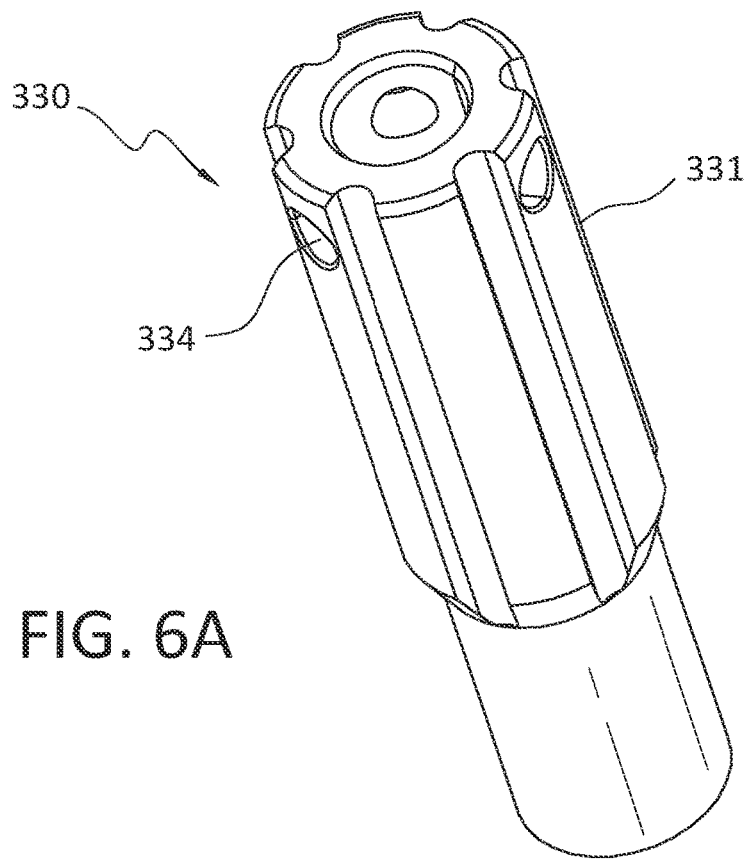
FIGS. 6A and 6B illustrate perspective and side cross-sectional views respectively of the tightening knob.
Figure 6B:
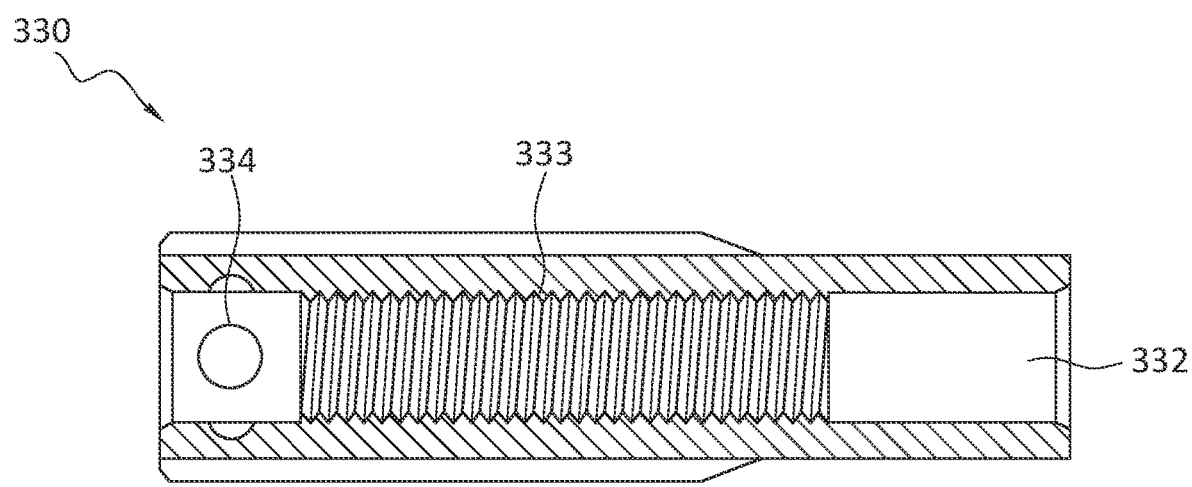

FIGS. 6A and 6B illustrate perspective and side cross-sectional views respectively of the tightening knob 330. The tightening knob 330 includes a grip 331 that the surgeon uses to turn the tightening knob 330. The grip 331 is shown as having a ridged surface, but other surfaces may be used that allow for the surgeon to securely grip and turn the tightening knob 330. The grip may also include wrench openings 334. In this example three wrench openings 334 are present, but more or fewer wrench openings 334 may be present. In order to tighten the sizing instrument 300 to the plate and bone during a sizing operation, the surgeon my place a hex wrench or other wrench into the wrench opening 334 in order to apply increased torque on the tightening knob 330. Not only does this secure the sizing instrument 300 to the bone and plate to provide an accurate size measurement, but it may also assist in compressing and reducing the bone fracture into place which also assists in accurate sizing of the attachment clamp 100. Accordingly the various elements will be sized and use materials that resist bending during the process due to the forces needed to reduce the bone. The outer diameter of the medial gauge 340 may range from a M5 to a M12 and the instrument may have a bending strength ranging from 7.65 mm$^3$ to 96.08 mm$^3$. The tightening knob 330 includes a gauge opening 332 which is a generally cylindrical opening through the length of the tightening knob 330 that is configured to be placed over, engage, and receive the medial gauge 340. The gauge opening 332 includes a threaded portion 333. The threaded portion 333 engages threads 343 on the medial gauge 340 (see FIGS. 7A-7F). The threaded portion 333 may be double-lead threaded in order to more quickly advance the tightening knob 330 as it is turned. In other embodiments, the threaded portion 333 may be single-lead, triple-lead, or quadruple-lead threaded.

Figure 7A:
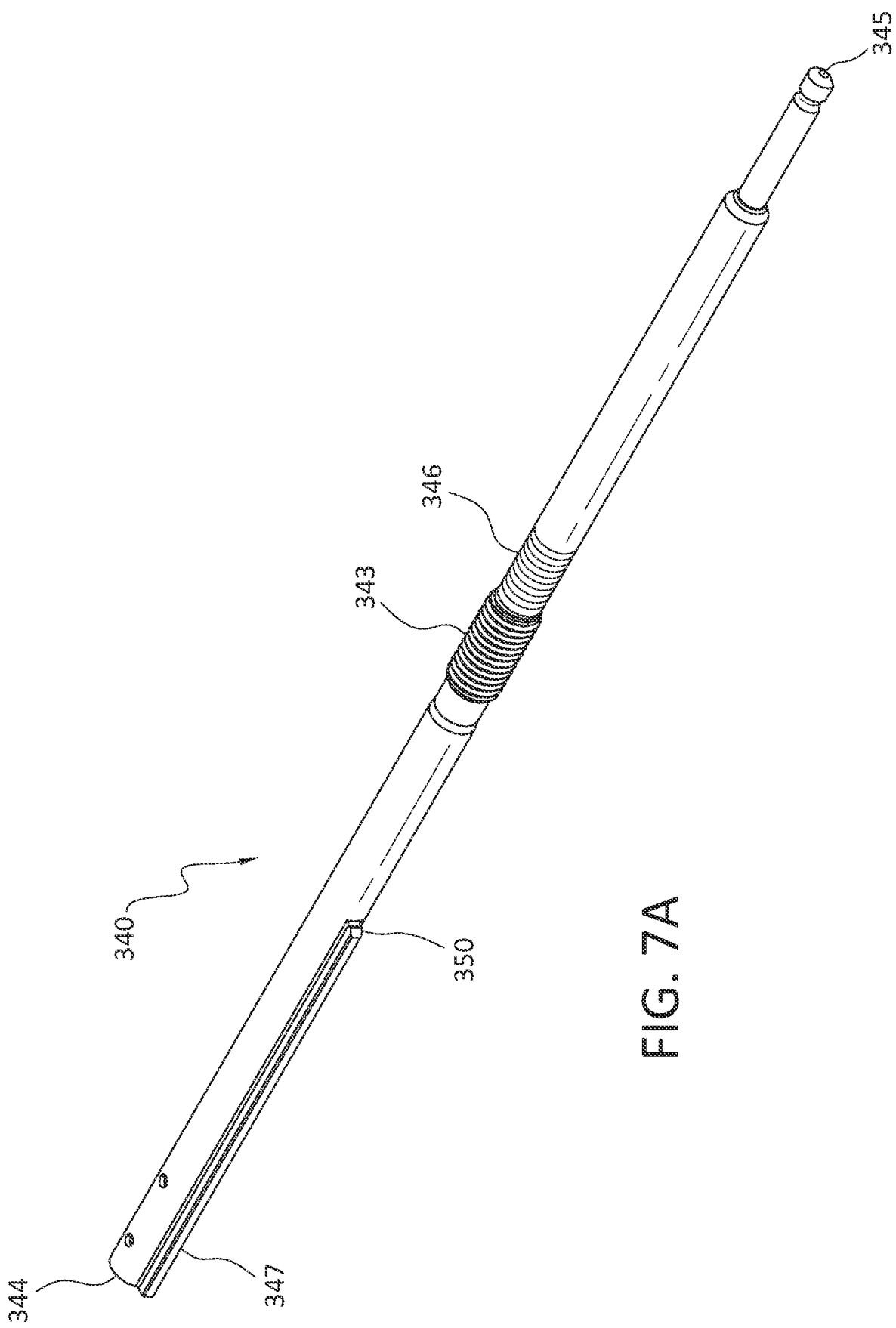

FIGS. 7A-7E illustrate various views of the medial gauge 340. FIGS. 7A, 7B, and 7C illustrate perspective, side, and top views respectively of the medial gauge 340. The medial gauge 340 has a proximal end 345 and a distal end 344. The proximal end 345 may include a standard AO quick connect interface to connect to a handle 360. Other connection schemes may be used as well. The medial gauge 340 is generally cylindrical with some variations along its length. As previously mentioned, a central portion of the medial gauge 340 includes a threads 343. The threads 343 engage the threaded region 333 of the tightening knob 330. Like the threaded region 333, the threads 343 may be double-lead threads in order to allow for the tightening knob 330 to advance more quickly when it is rotated. Alternative, the threads may be singe-lead, triple-lead, or quadruple-lead threaded.

The medial gauge 340 includes a gauge indicator 346 adjacent the threads 343 towards the proximal end 345 of the medial be gauge 340. FIG. 7D illustrates one embodiment of the gauge indicator 346 as a series of lines 348 with number labels 349. The lines 348 and the number labels 349 allow the surgeon to read off a measurement value from the gauge indicator 346 to then indicate the size of the attachment clamp 100 to use for a specific patient. In another embodiment, the gauge indicator 346 may be a series of colored bands, where each color indicates a specific size. In another embodiment, there may be lines indicating different sizes, for example small, medium, and large (S/M/L). For example, if there were three colored bands, the bands may correspond to a small, medium, and large sized attachment clamp 100. In such a case, the different sized attachment clamps 100 may have labeling that includes the color on the gauge indicator 346 to facilitate the selection of the correct size of attachment clamp 100.

As briefly mentioned above, the distal end of the medial gauge 340 may include a hollow end 341 configured to accept and engage the rod 322 of the medial arm 320. FIG. 7E is a cross-sectional view of the medial gauge 340 that better illustrates the hollow end 341. Further, there are holes 342 through the hollow end 341 that align with holes 323 in the rod 322 of the medial arm 320. Once the rod 322 is inserted in the hollow end 341, pins 324 may be inserted to affix the medial arm 320 to the medial gauge 340.

The medial gauge 340 also includes a key 347 that protrudes from the medial gauge 340. The key runs from the distal end 344 along a portion of the medial gauge 340 towards the threads 343. FIG. 7F is a cross-sectional view of the medial gauge 340 that is perpendicular to the length of the medial gauge 340. The section is taken through the key 347. As illustrated in FIG. 7F, the key 347 has as a largely rectangular shaped cross-section. The key 347 is configured to engage the channel 314 of the lateral arm 310. The key 347 may take other shapes a well, and the shape of the channel 314 corresponds to the shape of the key 347. When the channel 314 of the lateral arm 310 is engaged with the key 347 of the medial gauge 340, the lateral arm 310 is prevented from rotating around the medial gauge 340. If the lateral arm 310 is allowed to rotate round the medial gauge 340, it takes more effort for the surgeon to rotate the lateral arm 310 to the proper location as well as providing a distraction during use of the sizing instrument 300. Accordingly, the key 347 engaging with the channel 314 prevents this rotation and increases the ease of use of the sizing instrument 300.

The key 347 further has a key end 350. The cut out 315 on the lateral arm 310 is configured to be engaged with the key end 350 to hold the lateral arm 310 in place in an open position away from the medial arm 320 and out of the way during the initial use of the sizing instrument 300. As the cutout 315 is generally aligned with the arm member 312, the lateral arm 310 is rotated to align the cut out 315 with the key end 350. This rotates the arm member 312 to the side out of the way and away from the line of sight of the surgeon allowing the medial arm 320 to more clearly be seen during the initial placement of the sizing instrument 300.

Once the proper sized attachment clamp 100 has been selected, it must be implanted. In order to increase the ease of use and to successfully implant the attachment clamp 100, insertion instruments are needed.

Figure 8A:
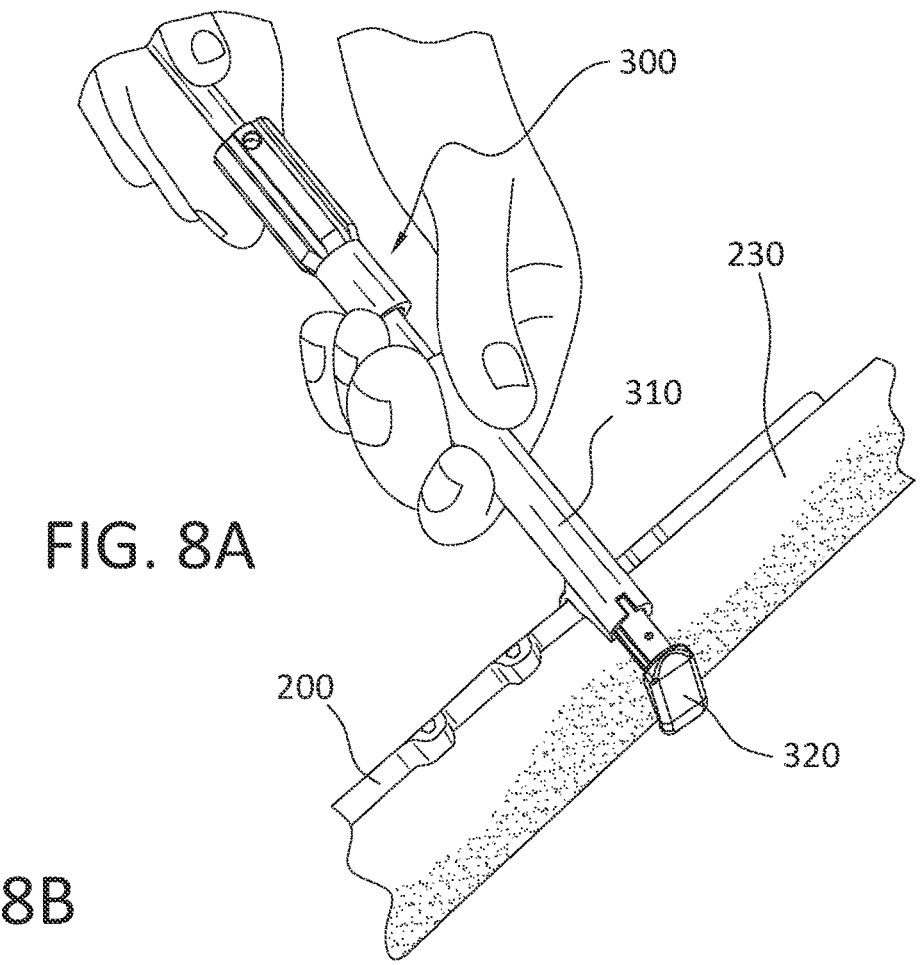
FIG. 8A illustrates the sizing instrument making initial contact with the plate.
Figure 8B:
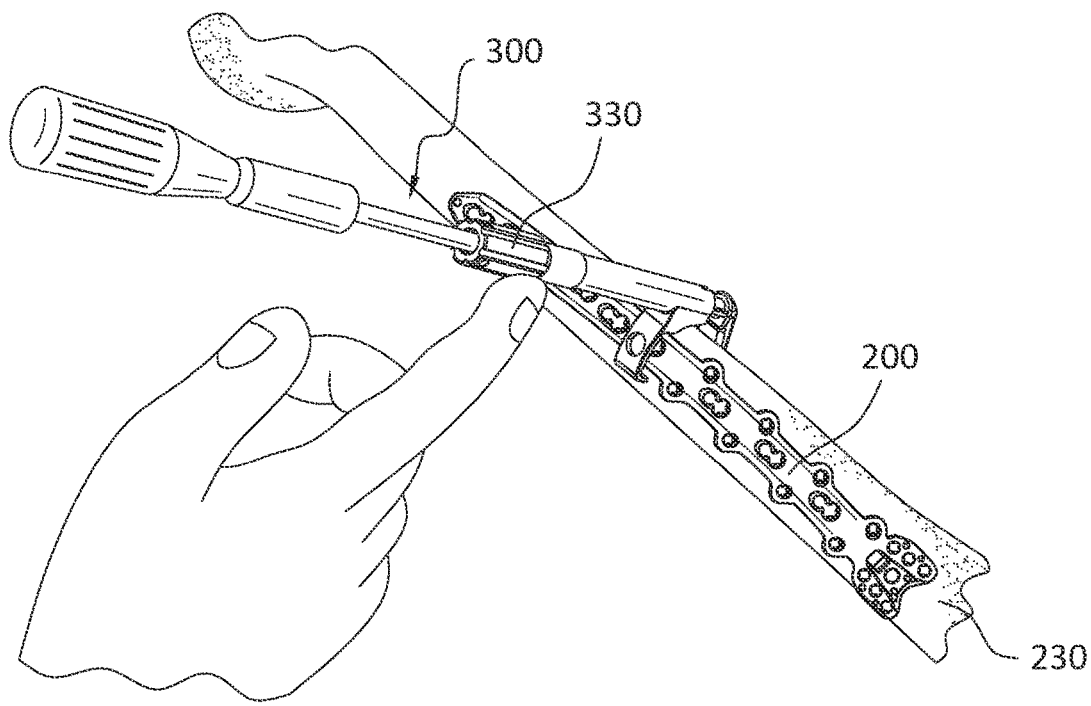
FIG. 8B illustrates the sizing instrument securely fixed to the bone and plate.

The process of sizing the attachment clamp 100 using the sizing instrument 300 will now be described. The surgeon first wraps the medial arm 320 of the sizing instrument 300 around the bone 230. Next, the lateral arm 310, which may be engaged out of the way using the cut out 315 and the key end 347, may be disengaged and rotated so that the channel 314 aligns with the key 347. The surgeon then slides the lateral arm 310 along the medial gauge 340 towards and into contact with the bone plate 200. In this situation the arm hole 316 allows the surgeon to see the plate 200 as the lateral arm 310 approaches and contacts the plate 200. FIG. 8A illustrates the sizing instrument 300 making initial contact with the plate 200. Then the surgeon rotates the tightening knob 330 so tighten the sizing instrument 300 on the bone 230 and plate 200. This tightening may help to reduce and compress the fracture of the bone 230. If additional torque is needed to tighten the measuring instrument 300, a wrench may be inserted in the wrench opening 334 and then used to rotate the tightening knob 330. FIG. 8B illustrates the sizing instrument 300 securely fixed to the bone 230 and plate 200. Once, the sizing instrument 300 is completely tightened, the surgeon may observe the gauge indicator 346 and, based upon the location of an end of the tightening knob 330 over the gauge indicator 346, read off the size. If the numbered indicator is used, then a size from 0 to 5 may indicate a small clamp, a size from 6 to 11 may indicate a medium clamp, and a size from 12 to 18 may indicate a large clamp. Alternatively, color bands may be used to indicate small, medium, and large clamps. Note, that more or fewer sizes may be indicated by the gauge indicator 346. Then the tightening knob 330 is loosened, the lateral arm 310 is slide away from the plate 200 and may be rotated to be stowed on the key end 350 using the cut out 315, and the medial arm 320 is removed from the bone 230 to remove the sizing instrument 300.

FIG. 9. illustrates an insertion instrument 400. The insertion instrument includes a connection rod 410, a provisional nut driver 430, and final nut driver 450.

FIG. 10 illustrates the connection rod. The connection rod has a proximal end 411 and a distal end 412. The proximal end 411 may include an AO interconnect 414 that may be connected to a handle 415 (see FIG. 14). The proximal end 411 may also be designed to have other types of connection interfaces. A threaded connector 413 is at the distal end 412. The threaded connector 413 is configured to be screwed into the stud opening 125 of the attachment clamp 100. This threaded connection provides a secure connection between the connection rod 410 and attachment clamp 100.

Figure 11A:
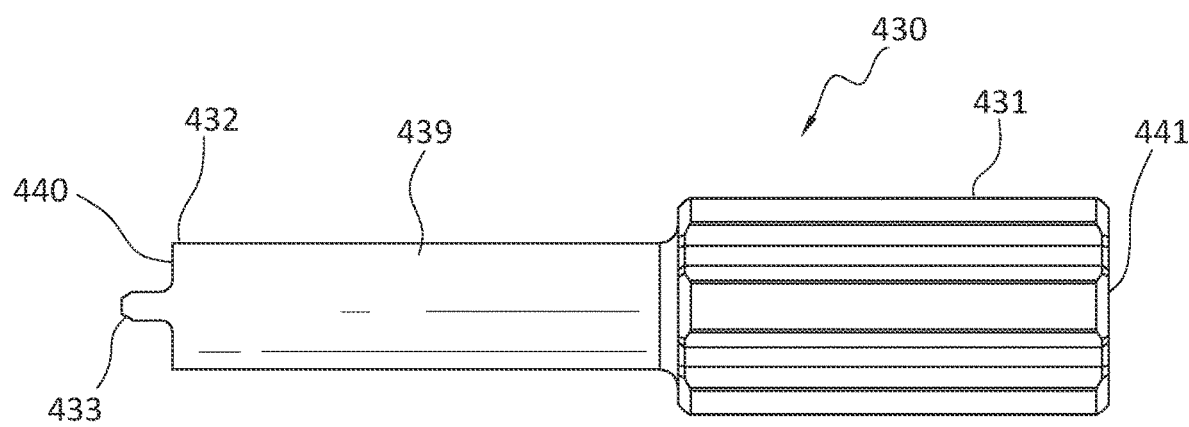
FIGS. 11A and 11B illustrate side and cross-sectional views respectively of the provisional nut driver.
Figure 11B:
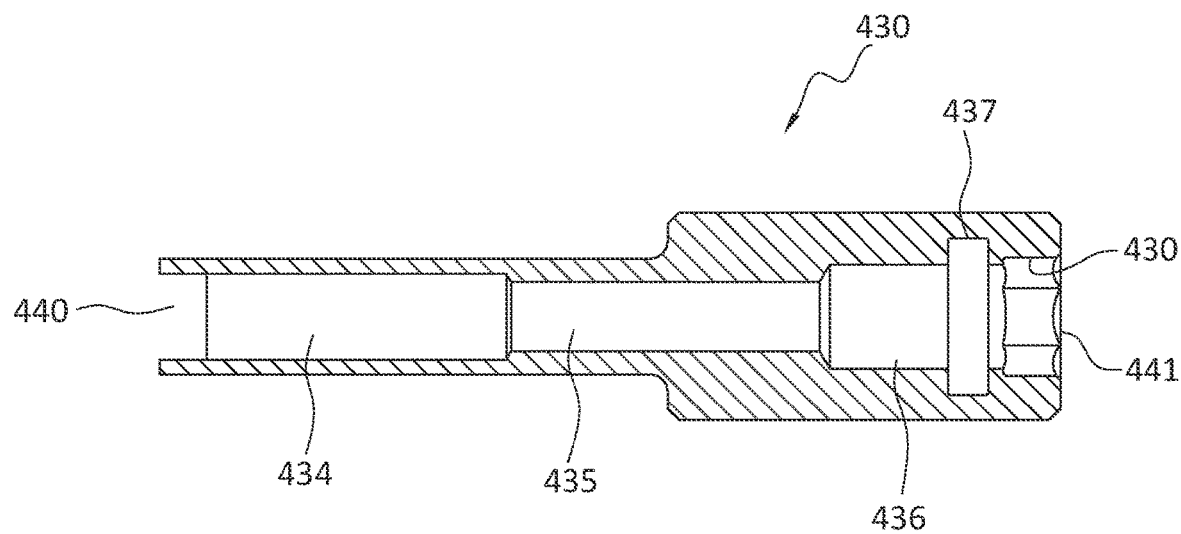
Figure 13B:
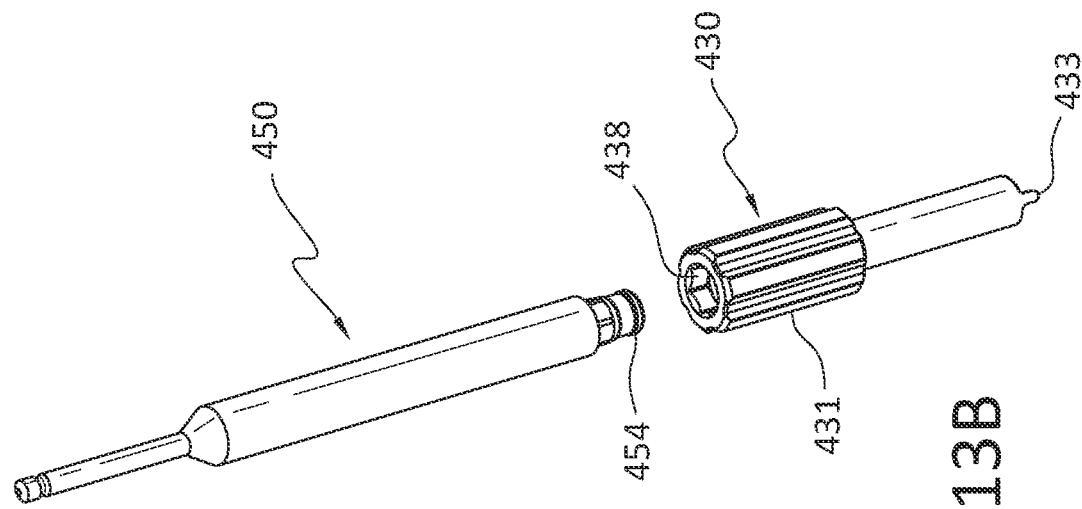
FIG. 13B illustrates a perspective view of the provisional nut driver and final nut driver separated from one another.

FIGS. 11A and 11B illustrate side and cross-sectional views respectively of the provisional nut driver 430. FIG. 13B also includes a perspective view of the provisional nut driver 430. The provisional nut driver 430 includes a handle 431 and a body 439. The handle 431 may have a larger circumference than the body 439, as the handle 431 is griped by the surgeon and rotated, and the larger diameter allows for easier grip and application of torque during rotation of the provisional nut driver 430. The grip may have ridges or other surface structures that improve the ability of the surgeon to securely grip and rotate the provisional nut driver 430 using the handle 431.

The provisional nut driver 430 has a distal end 432 that includes two tangs 433 and a distal opening 440. The tangs 433 are configured to engage the nut slots 131 on the nuts 130 and 132 used with the attachment clamp 100. While two tangs 433 and two nut slots 131 are shown, one, three or more tangs 433 and nut slots 131 may be used. Also the number of tangs 433 and nut slots 131 do not need to be the same, but rather the number of nut slots 131 should be a multiple of the number of tangs 433. For example, the nut 130 may include four or six nut slots 131 and the provisional nut driver 430 may have two tangs 433 that may engage pairs of nut slots 131 that are opposite one another. Other combinations are possible as well.

The provisional nut driver 430 is generally hollow with a number of different hollow sections including a first hollow section 434, a second hollow section 435, and a third hollow section 436. A first hollow section 434 in the body 439 extends from the distal opening 440 towards the handle 431. The diameter of this first hollow section 434 is set to fit over the stud 123 of the attachment clamp 100 because the provisional nut driver 430 will be placed over the stud 123 during insertion of the attachment clamp 100. Further, the tangs 433 are located at the end of the wall of the body that forms the first hollow section 434. The outer diameter of the body 434 and hence the location of the tangs 433 is set to allow for the tangs 433 to engage the nut slots 131.

The second hollow section 435 extends between the first hollow section 434 and the third hollow section of 436 as shown in FIG. 11B. The diameter of the second hollow section 435 is illustrated as being smaller than the diameter for the first hollow section 434, but in some cases they may be the same and hence, the first hollow section 434 and second hollow section 435 are actually a single section. The diameter of the second hollow section 435 is sized to be larger then the diameter of the insertion rod 410 which will extend into the second hollow section 435.

The third hollow section 436 is located between the second hollow section 435 and a spring channel 437. The third hollow section 436 has a diameter that corresponds to the outer diameter of a proximal end 451 of the final nut driver 450. As will be further discussed below, the proximal end 451 of the final nut driver 450 will be inserted into a proximal opening 441 and then the third hollow opening 436.

Figure 13A:
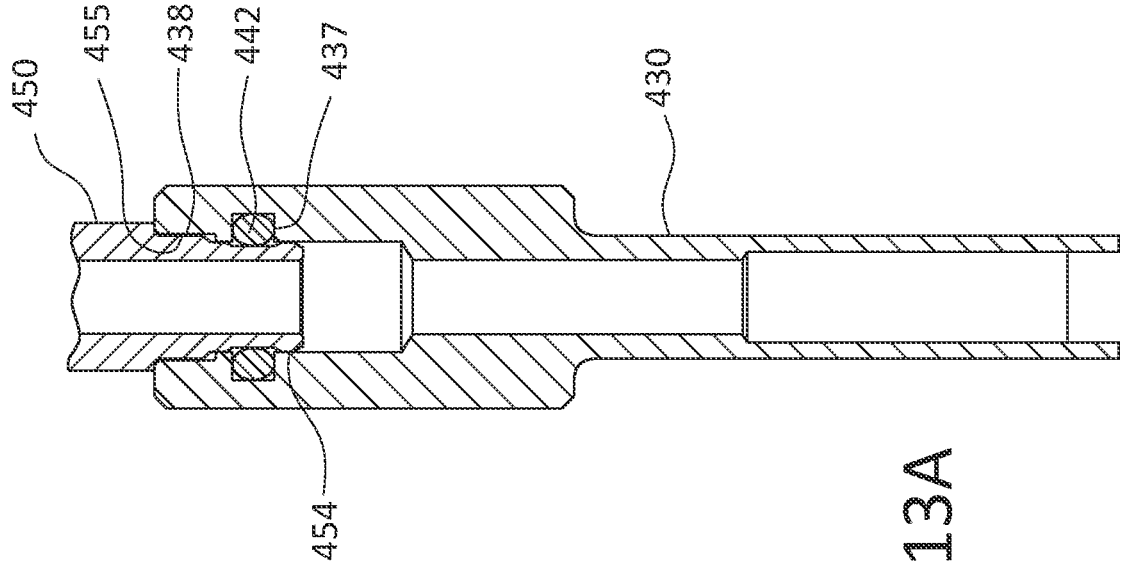
FIG. 13A illustrates a cross-sectional view of the provisional nut driver coupled to the final nut driver.

The spring channel 437 has a diameter greater than the diameter of the third hollow opening 436 in order to accommodate a spring 442 (see FIG. 13A). The spring 442 may be a coil spring. The spring 442 in the spring channel 437 will facilitate a quick connect functionality with the final nut driver 450. In another embodiment, a ball detent system may be used as well to implement this quick connection.

The provisional nut driver 430 also has a drive interface 438. In FIG. 11B, the drive interface is shown as having a hexagonal shape which interfaces with a hexagonal portion of the final nut driver 450. This creates a locked interface between the provisional nut driver 430 and the final nut driver 450 so that they rotate together. While a hexagonal interface is shown, any other shape that will allow the provisional nut driver 430 and the final nut driver 450 to be rotationally coupled may be used.

Figure 12A:
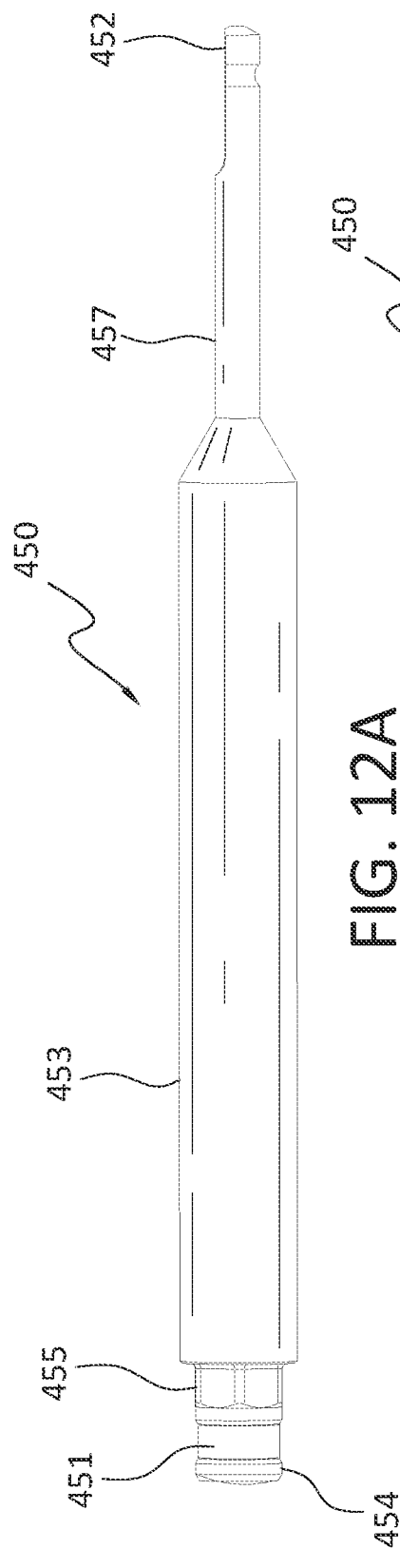
FIGS. 12A-12C are side and cross-sectional views respectively of the final nut driver.
Figure 12B:
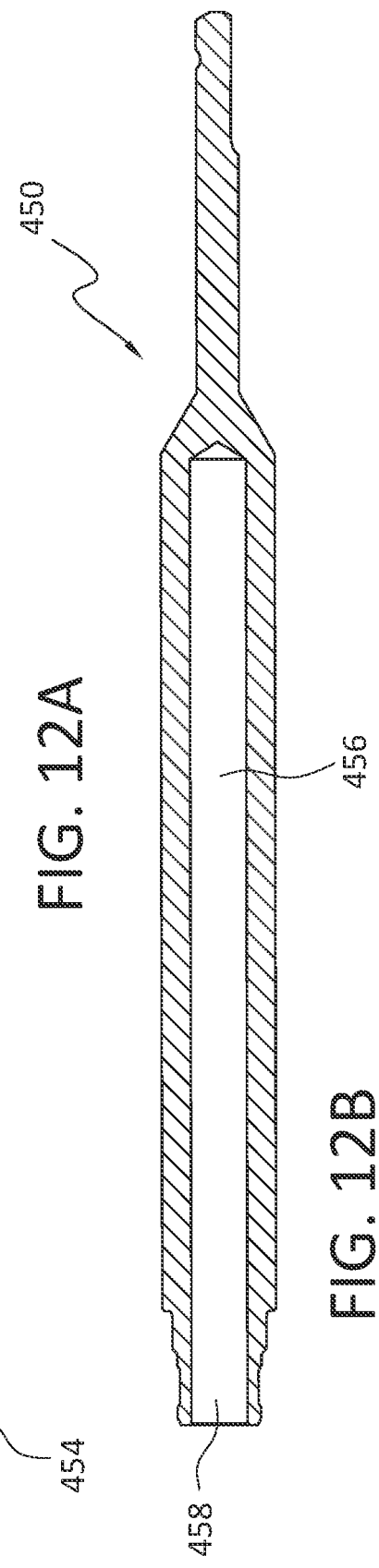
Figure 12C:
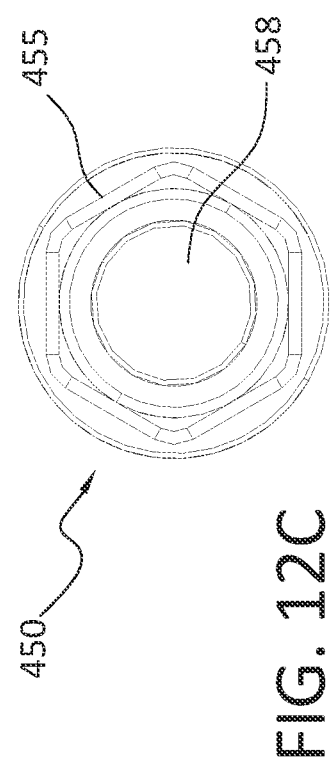

FIGS. 12A and 12B are side and cross-sectional views respectively of the final nut driver 450. FIG. 12C is an end view of a distal end of the final nut driver 450. Also, FIG. 13B illustrates a perspective view of the final nut driver 450. The final nut driver 450 may include a handle connector 457 at the proximal end 452. The handle connector 457 may include an AO quick connect interface or any other interface used by a handle. The handle connector 457 is connected to a body 453 of the final nut driver 450. The body 453 extends to the distal end 451 of the final nut driver 450. The body 453 is hollow with a final driver hollow section 456 and a final driver opening 458 at the distal end 451 of the final nut driver 450. During use of the final nut driver 450, the proximal end 411 of the connection rod 410 will be inserted into a final driver opening 458 and a final driver hollow section 456. Accordingly, the diameter for the final driver hollow section 456 is sized to accommodate the proximal end 411 of the connection rod 410.

The distal end 451 includes a ridge 454 and a final driver interface 455 that interfaces with the proximal nut driver 430. The ridge 451 interacts with the spring 442 to implement a quick connect capability between the final nut driver 450 and the provisional nut driver 430. Further, as previously discussed the final driver interface 455 engages the driver interface 438 of the provisional nut driver 430. In FIG. 12C, the final driver interface 455 is shown as hexagonal in shape, but the shape could take on any shape that will allow the provisional nut driver 430 and the final nut driver 450 to be rotationally coupled.

FIG. 13A illustrates a cross-sectional view of the provisional nut driver coupled to the final nut driver. FIG. 13B illustrates a perspective view of the provisional nut driver and final nut driver separated from one another. When the final nut driver 450 is coupled to the provisional nut driver 430, the ridge 454 slides past the spring 442 by compressing the spring 442. Once the ridge 454 is past the spring 442, the spring will cause the final nut driver 450 to be retained within the provisional nut driver 430 until sufficient pulling force is applied to separate them. As will be discussed below, this quick connect functionality helps in the ease of use related to the using the insertion instrument 400 to insert the attachment clamp 100 in a patient. Further, FIG. 13A illustrates the mating of the drive interface 438 of the provisional nut driver 430 with the final driver interface 455 of the final nut drive 450.

FIG. 14 illustrates an assembly 1400 including the attachment clamp, connection rod, provisional nut driver, and non-torque limiting handle. FIG. 15 illustrates an assembly 1500 including the attachment clamp, connection rod, provisional nut driver, final nut driver, second clamp nut, and torque limiting handle. The assemblies 1400 and 1500 may be used to insert the attachment clamp 100.

The process for inserting the attachment clamp 100 into a patient using the insertion instrument 400 will now be described. First the connection rod 410 is connected to the attachment clamp 100. This is accomplished by screwing the threaded connector 413 on the connection rod 410 into the stud opening 125 on the attachment clamp 100. Next, the provisional nut driver 430 is slid over the connection rod 410. It is noted that this step may also be done before the connection rod 410 is connected to the attachment clamp 100. Next, a handle 415 may be attached to the proximal end 411 of the connection rod 410 using the AO interconnect 414. Again, this step may be performed before the connection rod 410 is connected to the attachment clamp 100 or before the provisional nut driver 430 is slid over the connection rod 410. This results in the assembly 1400 shown in FIG. 14 that includes the attachment clamp 100, the connection rod 410, and the provisional nut driver 430.

The plate 200 is initially placed on the bone using k-wires or a reduction instrument. The surgeon uses the handle 415 to wrap the medial clamp 120 of the attachment clamp 100 to the medial side of the bone. Also, the lateral clamp 110 may be slid down the stud 123 to initially engage the plate 200. Next, the surgeon engages the nut 130 with the tangs 433 on the provisional nut driver 430, and rotates the handle 431 of the provisional nut driver 430 to initially tighten the attachment clamp 100. At this point the surgeon may align the screw hole 111 in the lateral clamp 110 with the screw hole 210 on the plate and insert the screw 211 and tighten the screw 211.

Then the surgeon removes the handle 415. The surgeon next attaches a torque limiting handle 416 to the handle connector 457 of the final nut driver 450. The final nut driver 450 is then slid over the proximal end 411 of the connection rod 410 into contact with the provisional nut driver 430, and the surgeon gently pushes the torque limiting handle 416 until the final nut driver 450 clicks into engagement with the provisional nut driver 430 resulting in assembly 1500. Now the surgeon rotates the torque limiting handle 416 to do the final tightening of the nut 130 to a specified torque. Finally, the torque limiting handle 416 and the final nut driver 450 are removed. Then the handle 415 is reattached to the proximal end of the connection rod 410, and the connection rod 410 is rotated to disengage it from the attachment clamp 100. Now the attachment clamp 100 is installed.

In another embodiment, two nuts 130 and 132 may be used to secure the attachment clamp 100. In this case, after the first nut 130 is torqued to the desired torque value, the torque limiting handle 416, the final nut driver 450, and the provisional nut driver 430 are removed as a combined assembly. Then a second nut 132 is slide over the connection rod 410 and threaded onto the stud 123. Then the combined assembly is reinstalled and used to tighten the second nut 132 to the desired torque using the final nut driver 450.

Alternatively, a second nut 132 may be added by removing the connection rod 410 from the attachment clamp 100, threading the second nut 132 onto the stud 123, and the reattaching the connection rod 410 and tightening the second nut as described above.

The use of a provisional nut driver 430 and a final nut driver 450 in a two step process helps to facilitate the proper installation of the attachment clamp 100 to the bone and the plate 200. The nut 130 is provisionally tightened using the provisional nut driver 130, and then the screw 211 connecting the lateral clamp of the attachment clamp 100 is inserted. This allows for final alignment for the attachment clamp 100 with the plate 200. Further, this adjustment may occur before the teeth 122 on the medial clamp have fully engaged the medial side of the bone. Further, this provisional tightening helps to secure the plate 200 and attachment clamp 100 to the bone so that any further adjustments may be made without needed to hold the insertion instrument 400. Now, the final nut driver 430 with the toque limiting handle 416 may be used to tighten the nut to its final torque. It also reduces the risk of improper application of the clamp if the clamp is torqued down before the screw 211 is properly inserted.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. An insertion instrument configured to insert a clamp on a bone and a plate, comprising:
    an attachment clamp including:
        a lateral clamp with a hollow opening;
        a medial clamp attached to a stud wherein the stud has a threaded opening; and the stud is located inside the hollow opening of the lateral clamp; and
        a first clamp nut on the stud, wherein the clamp nut has a nut slot;
    a connection rod with a distal end having a threaded connector configured to be screwed into the threaded opening of the stud;
    a provisional nut driver including:
        a central hollow opening configured to accept the connection rod therethrough:
        a tang at a distal end configured to engage the nut slot:
        an opening at a proximal end including a drive interface;

a spring channel in the central hollow opening; and
a spring in the spring channel; and
a final nut driver including:
   a body with a hollow opening configured to receive a proximal end of the connection rod;
   a ridge around the circumference of a distal end of the final nut driver configured to be inserted into the opening of the provisional nut driver;
   a final nut driver interface between the ridge and the body configured to engage the drive interface of the provisional nut driver; and
   a handle connector at a proximal end of the final nut driver.

2. The measuring instrument of claim 1, wherein the drive interface and the final nut driver interface have corresponding polygonal shapes.

3. The measuring instrument of claim 1, wherein the hollow opening has a first section configured to receive an end portion of the stud.

4. The measuring instrument of claim 1, wherein the hollow opening has a second section configured to receive the connection rod therethrough.

5. The measuring instrument of claim 1, wherein the hollow opening has a third section configured to receive a distal end of the final nut driver.

6. The measuring instrument of claim 1, wherein the hollow opening has a first section configured to receive an end portion of the stud, a second section configured to receive the connection rod therethrough, and a third section configured to receive a distal end of the final nut driver.

7. The measuring instrument of claim 1, wherein the attachment clamp includes a second clamp nut with a nut slot.

8. The measuring instrument of claim 1, further comprising a non-torque limiting handle configured to engage a proximal end of the connection rod.

9. The measuring instrument of claim 1, further comprising a torque limiting handle configured to engage the handle connector of the final nut driver.

10. A method of inserting an attachment clamp using an insertion instrument to clamp a plate to a bone, comprising:
   attaching a connection rod of the insertion instrument to a hollow opening in a stud of the attachment clamp;
   provisionally tightening a first nut of the attachment clamp using a provisional nut driver by engaging a tang on the provisional nut driver with a nut slot in the first nut and rotating the provisional nut driver;
   attaching a lateral clamp of the attachment clamp to the plate using a connector;
   attaching a final nut driver to the provisional nut driver; and
   tightening the first nut to a specified torque value by rotating a torque limiting handle connected to the final nut driver.

11. The method of claim 10, further comprising before attaching a final nut driver to the provisional nut driver, removing a non-torque limiting handle from a proximal end of the connection rod.

12. The method of claim 10, wherein attaching a lateral clamp of the attachment clamp to the plate using a connector further includes screwing a screw into the plate through an opening in the lateral clamp.

13. The method of claim 10, further comprising:
   removing an assembly including the torque limiting handle, the final nut driver, and the provisional nut driver;
   placing a second clamp nut with a nut slot over the connection rod onto the stud of the attachment clamp;
   replacing the assembly over the connection rod; and
   tightening the second clamp nut to a specified torque using the torque limiting handle.

* * * * *